(12) United States Patent
Coale

(10) Patent No.: US 8,343,229 B2
(45) Date of Patent: Jan. 1, 2013

(54) TEXTURED BONE BLOCK IMPLANTS

(75) Inventor: Bradford J. Coale, Vernon, NJ (US)

(73) Assignee: EBI, LLC, Parsippany, NJ (US)

( * ) Notice: Subject to any disclaimer, the term of this patent is extended or adjusted under 35 U.S.C. 154(b) by 236 days.

(21) Appl. No.: 12/838,117

(22) Filed: Jul. 16, 2010

(65) Prior Publication Data
US 2012/0016489 A1  Jan. 19, 2012

(51) Int. Cl.
A61F 2/28 (2006.01)

(52) U.S. Cl. .................... 623/23.5; 623/23.63

(58) Field of Classification Search ............... 623/23.5, 623/23.63
See application file for complete search history.

(56) References Cited

U.S. PATENT DOCUMENTS

| | | |
|---|---|---|
| 4,950,296 A | 8/1990 | McIntyre |
| 5,112,354 A | 5/1992 | Sires |
| 5,514,180 A | 5/1996 | Heggeness et al. |
| 5,702,449 A | 12/1997 | McKay |
| 6,025,538 A | 2/2000 | Yaccarino, III |
| 6,206,923 B1 | 3/2001 | Boyd et al. |
| 6,258,125 B1 | 7/2001 | Paul et al. |
| 6,277,149 B1 | 8/2001 | Boyle et al. |
| 6,432,436 B1 | 8/2002 | Gertzman et al. |
| 6,530,955 B2 | 3/2003 | Boyle et al. |
| 6,635,087 B2 | 10/2003 | Angelucci et al. |
| 6,855,167 B2 | 2/2005 | Shimp et al. |
| 7,179,299 B2 | 2/2007 | Edwards et al. |
| 7,662,184 B2 | 2/2010 | Edwards et al. |
| 7,670,384 B2 | 3/2010 | Kumar et al. |
| 2001/0010021 A1 | 7/2001 | Boyd et al. |
| 2005/0015147 A1 | 1/2005 | Schwardt et al. |
| 2005/0131548 A1* | 6/2005 | Boyer et al. ............... 623/23.63 |
| 2006/0149376 A1* | 7/2006 | Shimp et al. ............... 623/17.11 |
| 2006/0212036 A1* | 9/2006 | Bianchi et al. ............... 606/72 |

* cited by examiner

Primary Examiner — David Isabella
Assistant Examiner — Randy Shay
(74) Attorney, Agent, or Firm — Harness, Dickey

(57) ABSTRACT

Implantable pliable bone blocks comprising a solid block of cortical bone characterized by a length, width and thickness, having a first and a second face on opposite sides of the block. The first and second faces have a plurality slot features. The angle of incidence of the slot features of the first face and the x-axis and the angle of incidence of the slot features of the second face and the x-axis ($a_2$) are such that the slots would intersect if they were in the same plane. Methods are provided for making implantable pliable bone blocks.

25 Claims, 8 Drawing Sheets

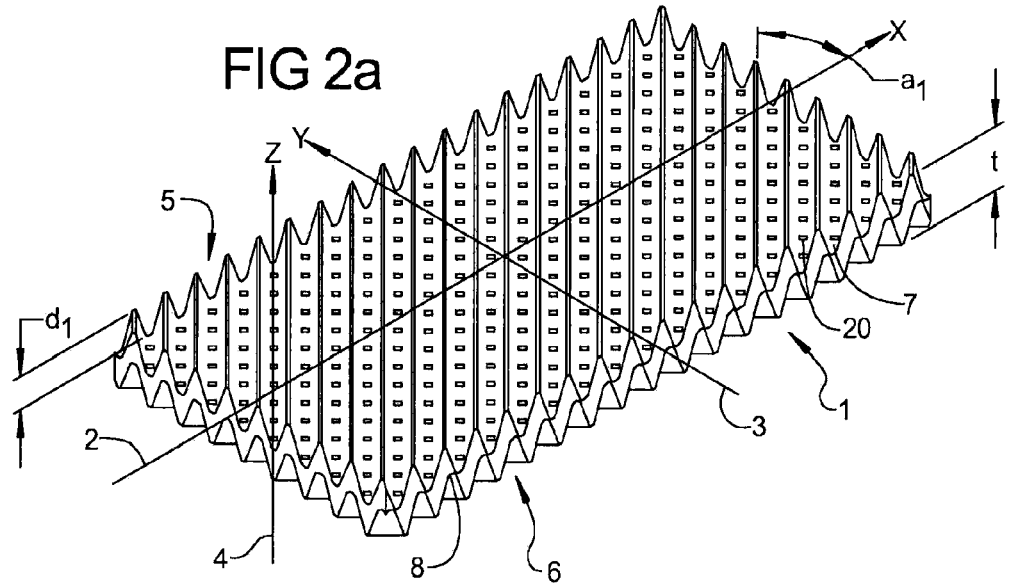
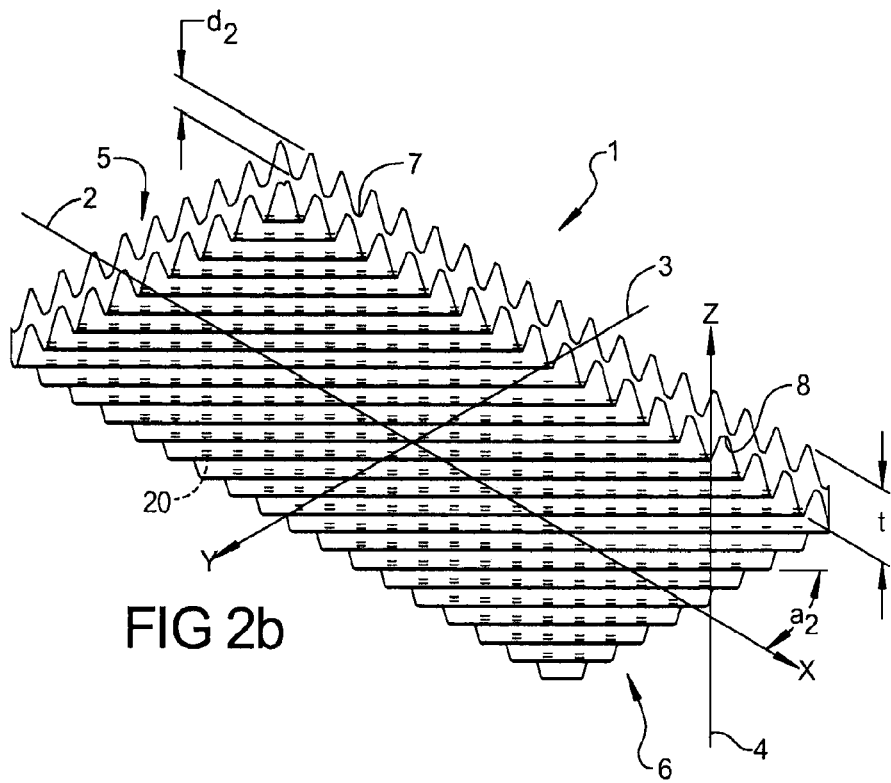

TEXTURED BONE BLOCK IMPLANTS

BACKGROUND

The present technology relates to implantable pliable bone blocks and methods of making implantable pliable bone blocks to treat bone defects and promote enhanced healing.

Osteogenesis and repairing of bone defects is a complex biological process requiring the concerted actions of bone forming cells such as osteoblasts and bone resorptive cells such as osteoclasts. The repair or reconstruction of bone defects may be aided by implants that initiate or enhance the formation of bone tissue. Such implants may be osteoconductive, osteoinductive, or both. In the case of a fracture or bone disease or defect, proper bone healing and subsequent bone remodeling is highly dependent on maintaining compatibility between osteoconductive materials that form the framework of the bone replacement and the osteoinductive materials which initiate replacement of the natural bone. Current bone graft materials include autografts (bone material obtained from the patient), allografts (the use of cadaver bone and bone material from human donors), xenografts (bone materials from non-human animals), and a variety of artificial or synthetic bone substitute materials.

An implantable bone block may be used to correct defects caused by trauma, pathological disease, surgical intervention or other situations where defects need to be managed in osseous surgery. Because defects are frequently jagged or irregularly shaped, it may be important for the block to be flexible and capable of numerous configurations for placement of the block into the site.

SUMMARY

In various embodiments, the present technology provides implantable pliable bone blocks, comprising a solid block of cortical bone characterized by a length (along an x-axis), width (along a y-axis) and thickness (along a z-axis), having a first face and a second face along the x and y axes on opposite sides of the block. Each of the first and second faces has a plurality of substantially linear and substantially parallel slot features, wherein the angle of incidence ($a_1$) of the slot features of the first face and the x-axis and the angle of incidence ($a_2$) of the slot features of the second face and the x-axis are such that the slot features of the first face would intersect the slot features of the second face if they were in the same plane. The blocks are preferably demineralized, for example being at least about 90% demineralized. The block may further comprise a bioactive agent, such as osteoinductive agents, stem cells, blood, and blood components.

The present technology additionally provides methods for making bone blocks, comprising: a) forming a block from cortical bone, the block characterized by a length (along an x-axis), width (along a y-axis) and thickness (along a z-axis), and having a first face and a second face along the x and y axes on opposite sides of the block; b) demineralizing the block; c) forming a plurality of slots on the first face of the bone block; d) forming a plurality of slots on the second face of the bone block; and e) wherein the angle of incidence ($a_1$) of the slot features of the first face and the x-axis and the angle of incidence ($a_2$) of the slot features of the second face and the x-axis are such that the slot features of the first face would intersect the slot features of the second face if they were in the same plane.

An advantageous feature of the present technology is a unique implantable cortical bone block that is pliable while resisting compression about its thickness. Such bone blocks can be implanted into the human body for numerous applications, for example as posterolateral fusion (PLF) procedures, or for electronic stimulation of bone growth.

BRIEF DESCRIPTION OF THE DRAWINGS

FIG. 2 shows top (2a) and bottom (2b) perspective views of an implantable pliable bone block having first and second face with a plurality of slot features, wherein the slot features include a plurality of holes.

FIG. 7a depicts a schematic view of the implantable pliable bone block which can be used to repair a vertebral bone injury; FIG. 7b depicts a schematic view of the implantable pliable bone block which can be used to promote bone growth using electrical stimulation; FIG. 7c depicts a schematic view of the multiple implantable pliable bone blocks which can be stacked to form a rigidity construct; and FIG. 7d depicts a schematic view of the implantable pliable bone block which can be collapsed to fit down a tube and used to repair a bone injury.

DESCRIPTION

Figure 1A:
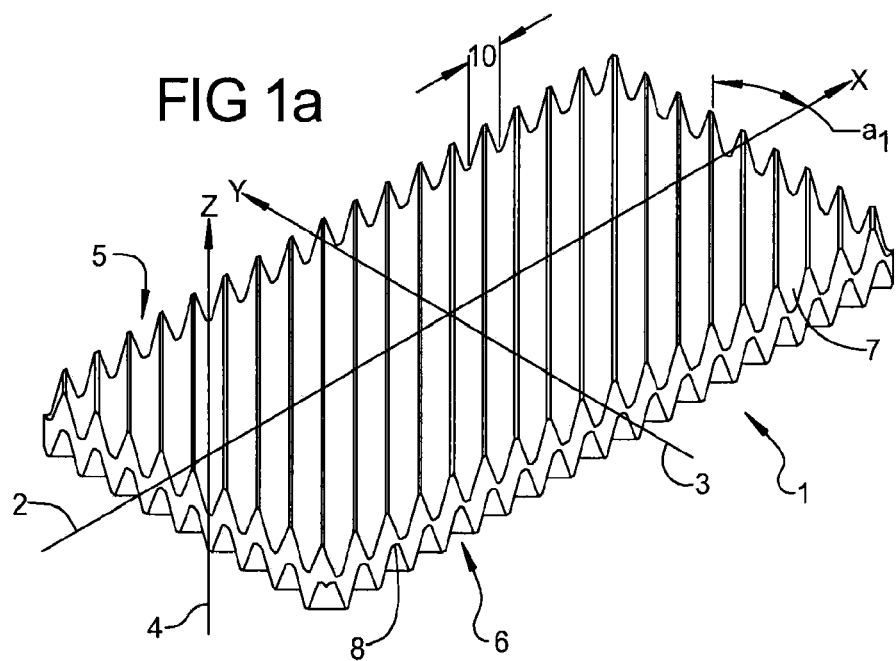
FIG. 1 shows top (1a) and bottom (1b) perspective views of an implantable pliable bone block having first and second faces including a plurality of slot features.

The following description of technology is merely exemplary in nature of the subject matter, manufacture and use of one or more inventions, and is not intended to limit the scope, application, or uses of any specific invention claimed in this application or in such other applications as may be filed claiming priority to this application, or patents issuing therefrom. A non-limiting discussion of terms and phrases intended to aid understanding of the present technology is provided at the end of this Detailed Description.

The present technology provides bone constructs and methods for making such constructs for the repair or treatment of bone defects. Such defects include any abnormality or other feature in bone constituting a structural or cosmetic defect. Such defects may result from injury or may be brought about during the course of surgery, osteoporosis, infection, malignancy or developmental malformation. Bone defects can also include bone breakages such as simple, compound, transverse, pathological, avulsion, greenstick and comminuted fractures. A bone defect may also be a void in the bone that requires filing with a bone graft composite of the present teachings. In various embodiments, the bone graft can be used to repair a bone defect through osteogenesis, the formation of new bone by the cells contained within the graft. Grafts may also repair defects by osteoinduction, a process in which materials contained within the graft (for example, bone morphogenetic proteins and TGF-β) convert the patient's or other bone progenitor cells into cells that are capable of forming bone. Grafts may also repair defects through osteoconduction, by which the graft forms a scaffold on which bone forming cells in the recipient are able to form new bone.

In various embodiments, the implantable pliable bone block of the present teachings provides conditions favorable for osteogenesis. Osteogenesis primarily involves two types of bone formation: the first is intramembranous bone formation; the second is endochondral bone formation. The difference between the two osteogenic processes revolves around the use of cartilage as the starting material for bone. Implantable pliable bone blocks described herein can be used to facilitate the replacement and filling of bone material in and around preexisting host bone. In some embodiments, the implants described herein can also be used to produce cartilage which is then mineralized to form bone. In some instances, mesenchymal stem cells present in the bone graft or at the site of implantation can differentiate into chondrocytes first, followed by deposition of extracellular matrix and invasion of blood vessels and other bone forming cells. Thus, the bone graft composites described herein can interact intimately with the surrounding bone tissue and blood vessels. Implantable pliable bone blocks described herein can provide for grafting materials that exhibit biocompatibility, i.e. the graft materials are not inflammatory and are conducive to cellular in-growth and differentiation of progenitor bone cells within the bone graft.

Furthermore, without being bound to theory, implantable pliable bone blocks of the present technology allow the host's circulating mesenchymal stem cells and the graft's embedded stem cells to produce new bone at the treated site (osteoinduction). Osteoinductive factors (e.g. BMPs and other growth factors) deposited or infused on the surfaces of the implantable pliable bone block (as discussed below) can attract circulating and embedded mesenchymal stem cells to the site of repair and provide the necessary differentiation signals to coordinate the differentiation of mesenchymal stem cells into bone forming and remodeling cells.

Cortical Bone Block

Figure 1B:
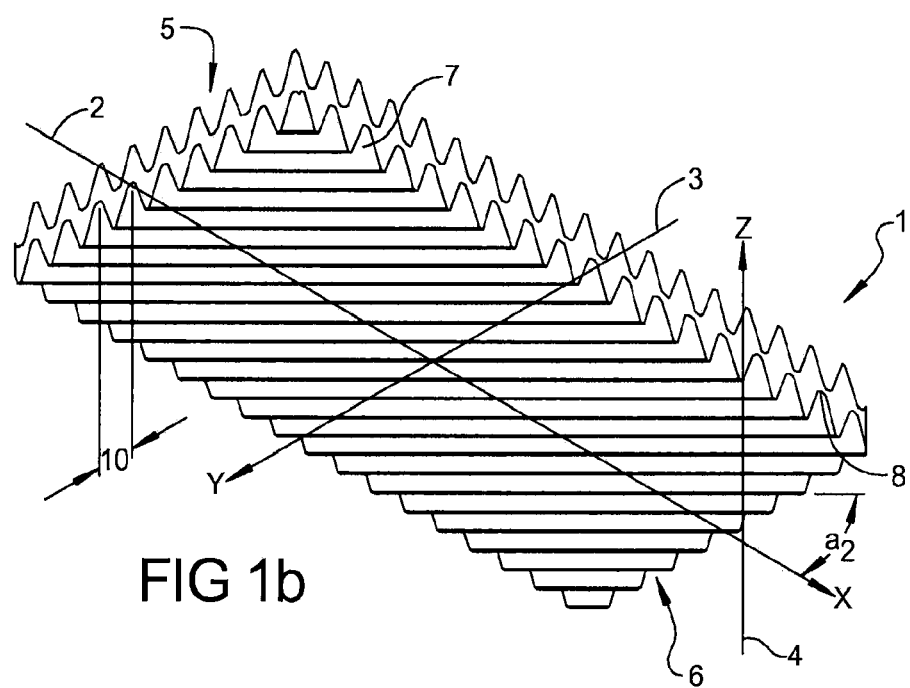

Referring to FIGS. 1a and 1b, the present technology provides implantable pliable bone blocks, comprising a solid block 1 of cortical bone characterized by a length (along an x-axis, 2); width (along a y-axis, 3); and thickness (along a z-axis, 4), having a first face 5 and a second face 6 along the x and y axes 2, 3 on opposite sides of the block 1, each of the first 5 and second 6 faces having a plurality of substantially linear and substantially parallel slot features 7, 8 wherein the angle of incidence ($a_1$) of the slot features 7 of the first face 5 and the x-axis 2 and the angle of incidence ($a_2$) of the slot features 8 of the second face 6 and the x-axis 2 are such that the slots 7, 8 would intersect if they were in the same plane. It should be understood that term "block" and references to x-, y-, and z-axes are for descriptive convenience, and are not intended to limit three-dimensional geometric characteristics of the "block" constructs of the present technology. Thus, the blocks 1 of the present technology may have any shape suitable for implantation, depending on such factors as the defect to be repaired and the surgical technique to be employed. Accordingly, as discussed further below, the blocks 1 may have a specific geometric shape (such as a block, disc, patch, ring or cylinder), may be irregularly shaped, or may have a site-specific shape to fit a specific site for bone repair. In general, the bone blocks 1 may be from 5 mm to 100 mm in length (along the x-axis 2), from about 5 mm to 50 mm in width (along the y-axis 3), and from about 3 mm to about 12 mm in thickness (along the z-axis 4). It is understood, however, the blocks 1 may have length, width, and thickness outside of these ranges, depending on the desired evidence of the block. Moreover, the terms "length", "width", and "thickness" are understood to be relative, and are not meant to imply a specific geometry.

The bone used in the blocks 1 may be obtained from any natural bone. The bone may be cortical of autogenic, allogeneic, or xenogeneic in origin with respect to the subject in whom the block is to be implanted. Preferably, the bone is autologous bone or donated from a single member of the same species as the patient to reduce or prevent an immunogenic response. In various embodiments, the bone material is a solid block of cortical bone, harvested, for example, from a femur of a donor subject. The cortical bone block may be further processed by various techniques known in the art to remove substantially all blood and lipid residue.

The compositions of the present technology comprise demineralized cortical bone. The term "demineralized" as used herein refers to bone containing less than its original mineral content and is intended to encompass "substantially demineralized", "partially demineralized", and "fully demineralized" bone material. The demineralized cortical bone can be produced by acid extraction, thermal freezing, irradiation, physical extraction of inorganic minerals of human or animal bone. The strength of the acid solution and the duration of the demineralization treatment will determine the extent of demineralization. In various embodiments, the bone is at least 99%, at least 95%, at least 90%, at least 80%, at least 70%, or at least 50% demineralized.

The implantable bone blocks are preferably pliable. The pliability of implantable bone block may depend on the extent of demineralization. In general, lesser degrees of demineralization will result in greater stiffness of the implants. The more demineralized the cortical bone block 1 is, the softer and more pliable the block will be while resisting compression about its thickness.

A demineralized cortical bone block retaining its native osteoinductive factors may be used. In various embodiments, a bioactive agent can be deposited on a surface of the bone block 1. Such agents may be applied as a coating on one or more surfaces of the block, or infused into the block. Bioactive agents can include any natural, recombinant or synthetic compound or composition that promotes the growth of bone directly or indirectly. Bioactive agents among those useful herein include isolated tissue materials, growth factors and other cytokines and hormones, pharmaceutical actives, and combinations thereof. Isolated tissue materials include, for example, whole blood and blood fractions (such as red blood cells, white blood cells, platelet-rich plasma, and platelet-poor plasma), bone marrow aspirate and bone marrow fractions, lipoaspirate and lipid-derived materials, isolated cells and cultured cells (such as hemopoietic stem cells, mesenchymal stem cells, endothelial progenitor cells, fibroblasts, reticulacytes, adipose cells, and endothelial cells). Growth factors and cytokines useful herein include transforming growth factor-beta (TGF-β) including the five different subtypes (TGF-β1-5); bone morphogenetic factors (BMPs, such as BMP-2, BMP-2a, BMP-4, BMP-5, BMP-6, BMP-7 and BMP-8); platelet-derived growth factors (PDGFs); insulin-like growth factors (e.g., IGF I and II); and fibroblast growth factors (FGFs), vascular endothelial growth factor (VEGF), osteocalcin, osteopontin, and combinations thereof. Examples of pharmaceutical actives include antimicrobials, chemotherapeutic agents, and antiinflammatories. Examples of antimicrobials include sulfonamides, furans, macrolides, quinolones, tetracyclines, vancomycin, cephalosporins, rifampins, and aminoglycosides such as tobramycin and gentamicin.

Referring again to FIGS. 1a and 1b, the faces of the bone block 1 of the present technology comprise a plurality of substantially parallel linear slot features 7, 8 extending below the surface of the first 5 and second 6 faces of the bone block.

In various embodiments, the slots 7, 8 may have a substantially V- or U-cross section profile. The number and orientation of the slot features may affect the handling characteristics of the blocks, such as expansion, elongation, collapsibility or bendability. In various embodiments, the distance 10 between the slot features 7, 8 on each of the first face 5 and the second face 6 is from about 0.5 mm to about 3 mm.

Referring now to FIGS. 2a and 2b, in various embodiments the slot features 7, 8 include a plurality of holes 20 having a diameter of from about 0.5 mm to about 2 mm at the intersections of the slot features 7 of the first face 5 and the slot features 8 of the second face, 6. The number and size of the plurality of holes 20 depend on the number of slot features 7, 8, the angles $a_1$ and $a_2$, and the thickness (along the z-axis, 4) of the bone block 1. Referring now to FIGS. 2a and 2b, in various embodiments, the slot features 7, 8 are characterized by a depth substantially along the z-axis 4, wherein the sum of depth ($d_1$) of the slot features 7 on the first face 5 and the depth ($d_2$) of the slot features 8 on the second face 6 is greater than the thickness (t) of the block 1. For example, the plurality of holes 20 will be formed if the slot features 7, 8 on both faces 5, 6 are more than 50% of the thickness (t) of the cortical block 1. If the slot features 7, 8 of both faces 5, 6 are less than 50% of the thickness (t) of the cortical block 1, the slot features 7, 8 will not intersect at the x-axis and the plurality of holes 20 will not be formed (e.g., as shown in FIG. 1).

Figure 3A:
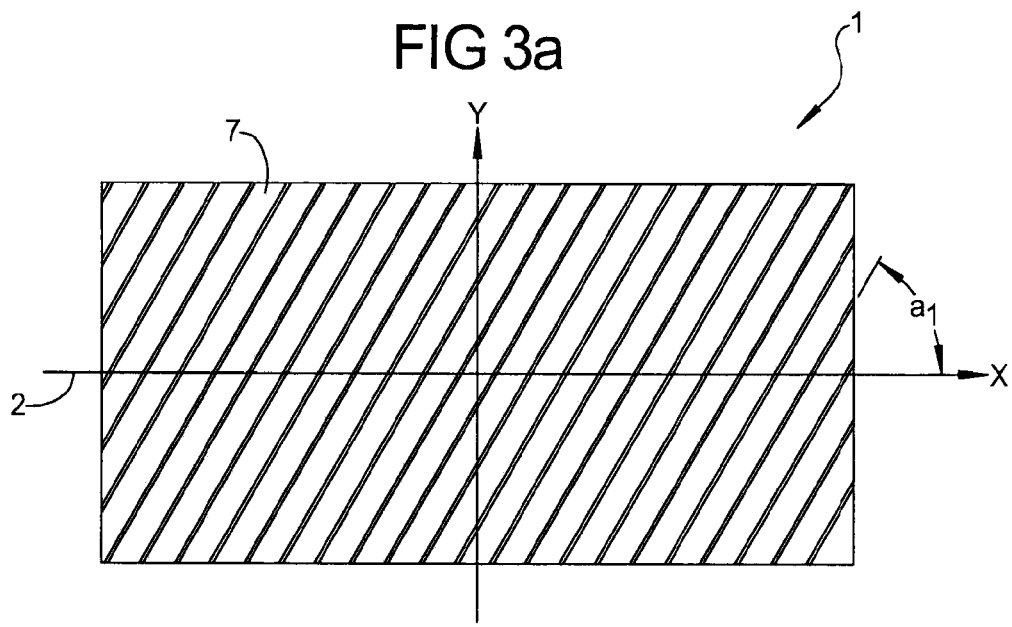
FIGS. 3a and 3b are top planar views of an implantable pliable bone block, which is expandable along the x-axis.
Figure 3B:
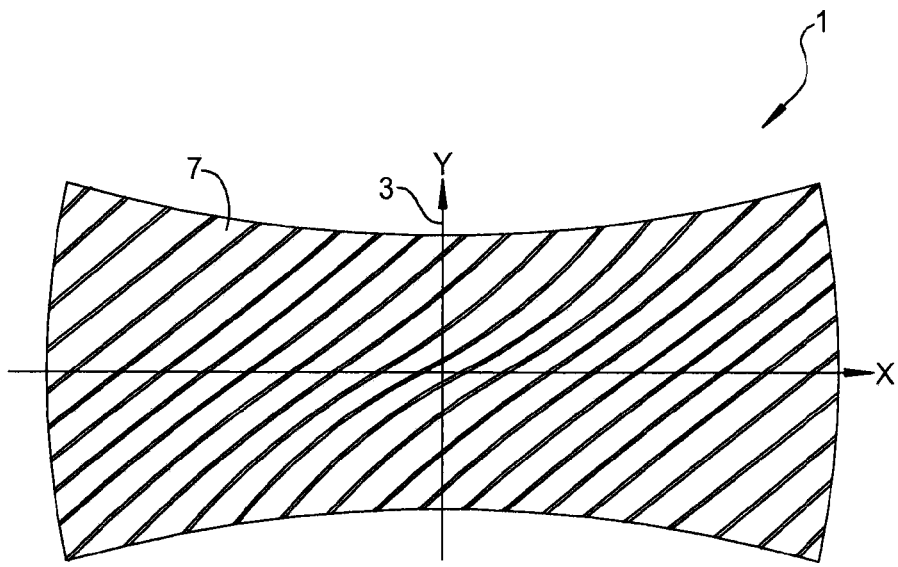
Figure 4A:
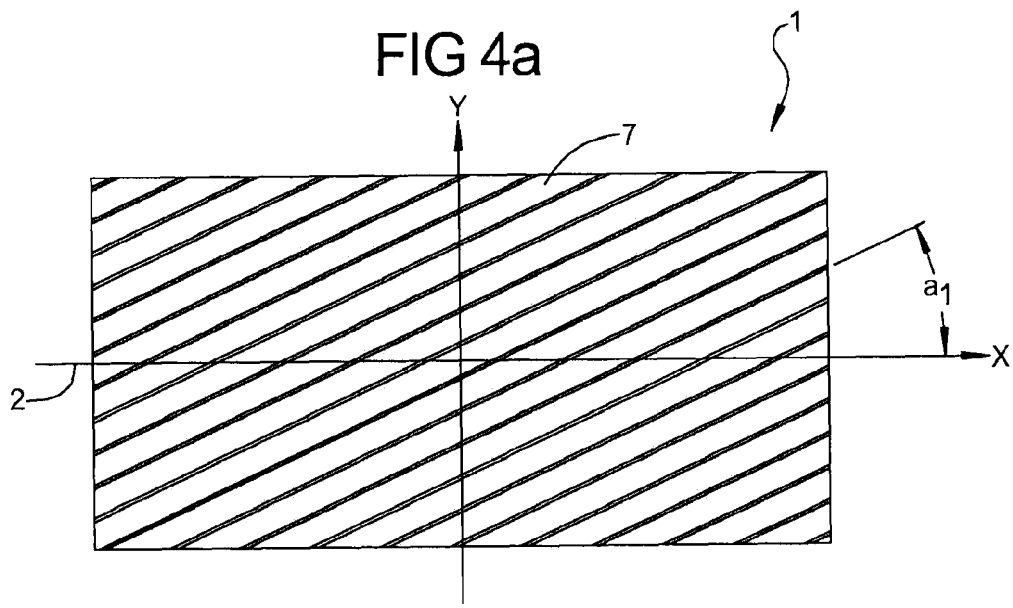
FIGS. 4a and 4b are top planar views of an implantable pliable bone block, which is expandable along the y-axis.
Figure 4B:
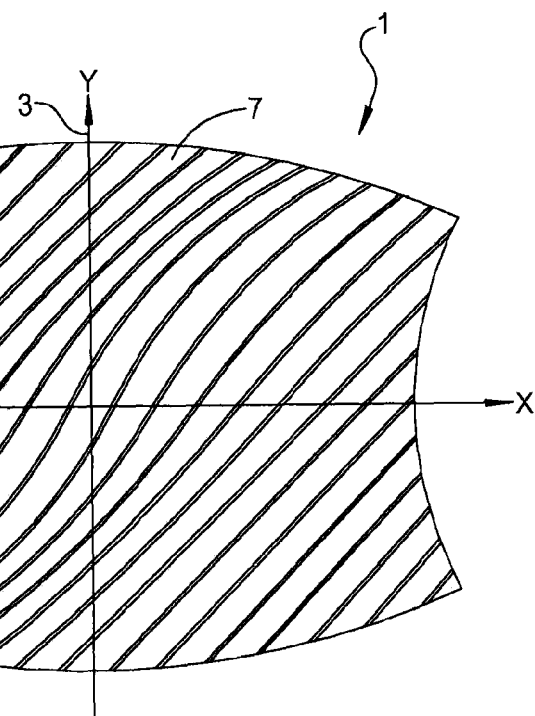
Figure 5:
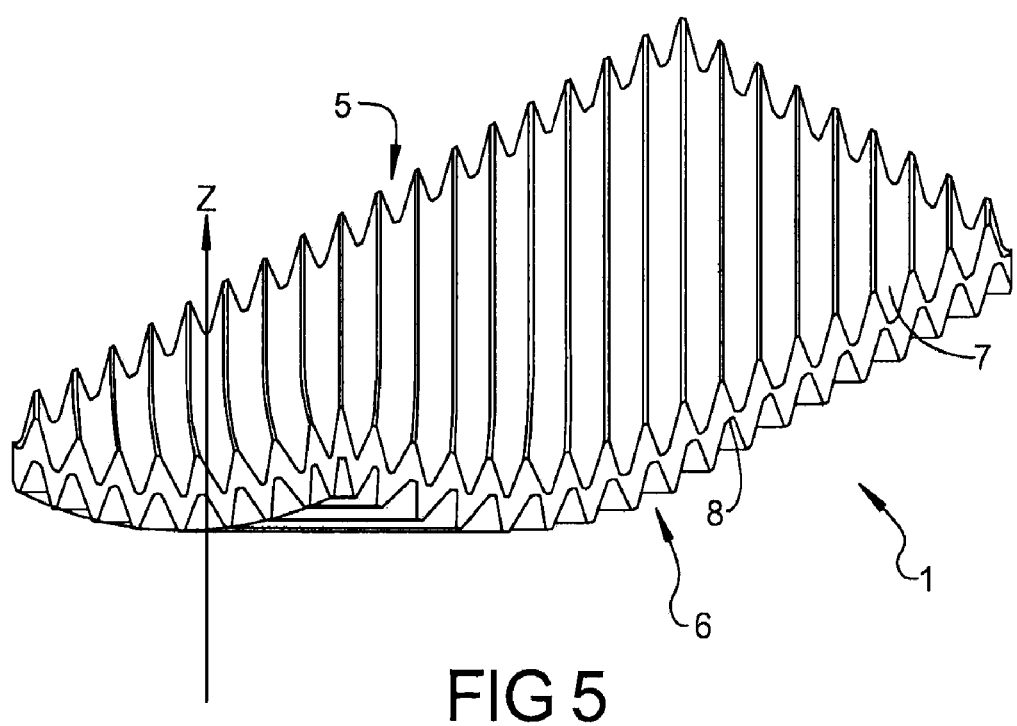
FIG. 5 is a perspective view of an implantable pliable bone block, depicting flexibility in the z-axis.

Referring again to FIG. 1, in various embodiments, the pliability of the implantable bone block may be altered. In general, angles $a_1$ and $a_2$, which may be the same or different, can range from about 0° to about 90°, more typically from about 10° to about 75°. An implantable bone block which is more pliable or less pliable may be accomplished by changing the number of slots 7, 8 and the degree at which the angles $a_1$ and $a_2$ are formed on the first 5 and second 6 faces. For example, in various embodiments, angles $a_1$ and $a_2$ are from about 35° to about 55° relative to the x-axis 2 of the bone block 1 and will generally expand equally along the x-axis 2 and y-axis 3, yielding a slightly more rigid but flexible implant. For example, in various embodiments as illustrated in top planar view in FIGS. 3a and 3b, angle $a_1$ and angle $a_2$ (not shown) of the slot features 7 may be from about 50° to about 75° incident to the x-axis 2 (for example, wherein $a_1$ is about 60° as depicted in FIG. 3a) to yield a flexible implant that expands (shown in FIG. 3b) along the x-axis 2. The block 1 may also compress along the x-axis 2. In various embodiments as illustrated in the top planar view in FIGS. 4a and 4b, angle $a_1$ (shown) and angle $a_2$ (not shown) of the slot features 7 may be from about 10° to about 35° incident to the x-axis 2 (for example, wherein $a_1$ is about 25° as depicted in FIG. 4a) to yield a flexible implant that elongates along the y-axis 3 (shown in FIG. 4b). The block 1 may also compress along the y-axis 3. The block may also be pliable (bendable) in the z-direction 4 as shown in perspective view in FIG. 5.

Methods of Preparation and Use of Implantable Pliable Bone Blocks

The present technology provides a method of making an implantable pliable bone block. In various embodiments, the methods comprise:

a) forming a block from cortical bone 1, the block by a length (along an x-axis 2), width (along a y-axis 3) and thickness (along a z-axis 4), having a first face 5 and a second face 6 along the x and y axes 2, 3 on opposite sides of the block 1;

b) demineralizing the block 1;

c) forming a plurality of slots 7 on the first face 5 of the bone block 1; and d) forming a plurality of slots 8 on the second face 6 of the bone block 1;

e) wherein the angle of incidence ($a_1$) of the slot features 7 of the first face 5 and the x-axis 2 and the angle of incidence ($a_2$) of the slot features 8 of the second face 5 and the x-axis 2 are such that the slots 7, 8 would intersect if they were in the same plane.

Figure 6A:
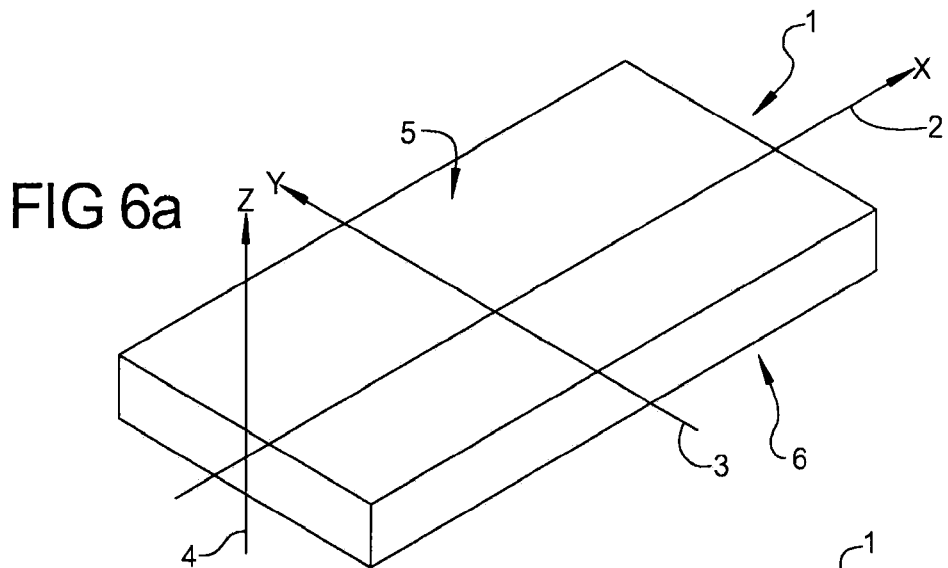
FIGS. 6a-6c illustrate steps in a method of manufacture of an implantable pliable bone block.

Referring now to FIG. 6a, the implantable pliable bone block can be formed by forming a block 1 from cortical bone, the block 1 characterized by a length (along an x-axis 2), width (along a y-axis 3), and thickness (along a z-axis 4), having a first face 5 and a second face 6 along the x- and y-axes 2, 3 on opposite sides of the block 1. Cortical bone is collected from a donor source and may include the entire bone or bone fragments from cortical bone. In a preferred embodiment, the subject is of the same species as the donor. For example, all of the bone used to prepare a composition for a human patient may be sourced from a single human cadaveric donor. Any adherent tissues may be removed from the bone by standard bone cleaning protocol.

As discussed above, the implantable pliable bone blocks of the present technology are not limited to any specific shape. The blocks 1 may have a specific selected geometric shape, such as blocks, rounded blocks, discs, patches, rings, cylinders, V-shapes, or the blocks may have a site-specific shape to fit the injury site.

The cortical bone block 1 may be defatted by soaking or washing the bone in ethanol. The ethanol solution is at least 60%, preferably 100%, ethanol, volume to volume, in deionized/distilled water. The ethanol bath also disinfects the bone by killing vegetative microorganisms and viruses. A further antiseptic step may include treatment of the cortical bone with a hydrogen peroxide solution.

The bone may be demineralized using an acidification or chelating process. Acids used include inorganic acids such as hydrochloric acid or organic acids such as peracetic acid. Chelating agents include disodium ethylenediaminetetraacetic acid ($Na_2EDTA$).

The time required to demineralize the bone may vary depending on the concentration of acid or chelating agent used, the displacement or flow of the solution, and the desired final concentration of calcium in the bone. For example, in an embodiment using hydrochloric acid, at an acid concentration of 0.1 to 2.0 N, the bones may be soaked in the acid bath for up to 24 hours. The calcium or mineral concentration in the cortical bone may be monitored by measuring the pH of the acid solution using a calcium specific electrode or a standard pH meter. In a preferred embodiment, the acid wash or soak ceases when the calcium concentration of the bone is less than 1%. In some embodiments, a demineralized solid cortical bone block is at least about 50% to about 100% demineralized. As discussed above, the more demineralized the cortical bone block is, the softer and more pliable the block becomes while resisting compression about its thickness.

After demineralization, the pH of the bone may be adjusted by removing the acid with a deionized/distilled water wash until the pH of the bone approximates that of the water. An ionic strength adjuster, such as a biocompatible buffer solution, may be used.

Figure 6B:
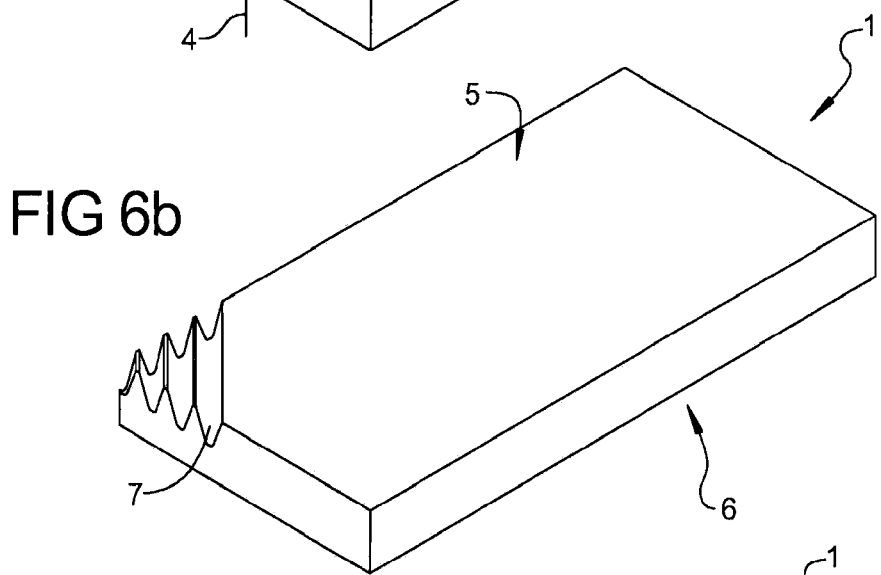
Figure 6C:
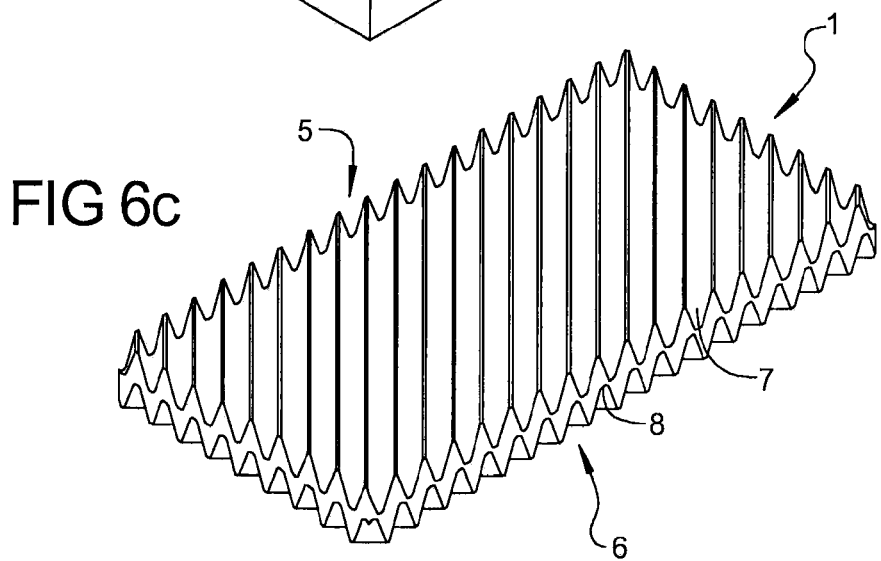

Referring to FIGS. 6b and 6c, a plurality of slot features 7, 8 is formed on the first and second faces 5, 6. The slot features 7, 8 may be formed by any suitable technique, including those known in the art for forming or milling solid materials and suitable for use with bone. For example, slot features may be formed on the cortical bone block using standard CNC (computed numerically controlled) milling technology, adaptive CNC milling technology, drills, or saws. In some embodiments, CNC milling technology is used to form the slot features 7, 8 by forming all the slot features 7 of the first face 5 (as shown in FIG. 6a) and then forming all the slot features 8 of the second face 6 (not shown), but in no particular order in regard to the first or second face 5, 6. In some embodiments, CNC adaptive milling technology is used to form to form the slot features 7, 8 and may shape the implantable pliable bone block 10 to the shape of implant location.

As discussed above, bioactive agents may be deposited on the surface of the bone block 1. Deposition of bioactive agents may be performed, for example, by dipping the implantable pliable bone block into a liquid solution, by infusing liquid into some or all of the bone block or by coating or bonding some or all of the bone block.

The bone block 1 may be dried, using standard drying techniques such as lyophilization. Preferably, the moisture level of the dried block is 6% or less. The block may be packaged under sterile conditions for storage and shipment, as needed.

Methods of Use

As discussed above, the bone blocks 1 of the present technology may be used in the treatment or repair of bone defects in a human or other animal subject. The blocks may be shaped during manufacture or intra-operatively to a desired shape and size. For example, the implant can be configured for percutaneous implantation; placement in posterolateral gutters or onlay fusion grafting in posterolateral fusion (PLF) procedures; filling interbody fusion devices/cages (ring cages, cylindrical cages), placement adjacent to cages (i.e., in front cages); backfilling of the iliac crest, acetabular reconstruction and revision of hips and knees, filling of large tumor voids, use in high tibial osteotomy, burr hole filling; external or internal bone graft containment; or repair or replacement of ethmoid, frontal, nasal, occipital, parietal, temporal, mandible, maxilla, zygomatic, cervical vertebra, thoracic vertebra, lumber vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones.

In various embodiments as discussed above, the bone block is dried (e.g., by lyophilization) during manufacture, and then rehydrated during implantation. Hydration may be effected before, during, or after implantation using any suitable biocompatible liquid, such as saline or fluid materials obtained from the surgical subject. For example, hydration may be accomplished with isolated tissue materials as discussed above, such as blood, bone marrow aspirate, adipose tissue liposuction aspirate or combinations thereof. Autologous or allogeneic bone marrow or adipose tissue liposuction aspirate can be collected as part of the donor's standard medical care prior to surgery. In some embodiments, the bone block becomes pliable when hydrated, yet still retains its shape.

Figure 7A:
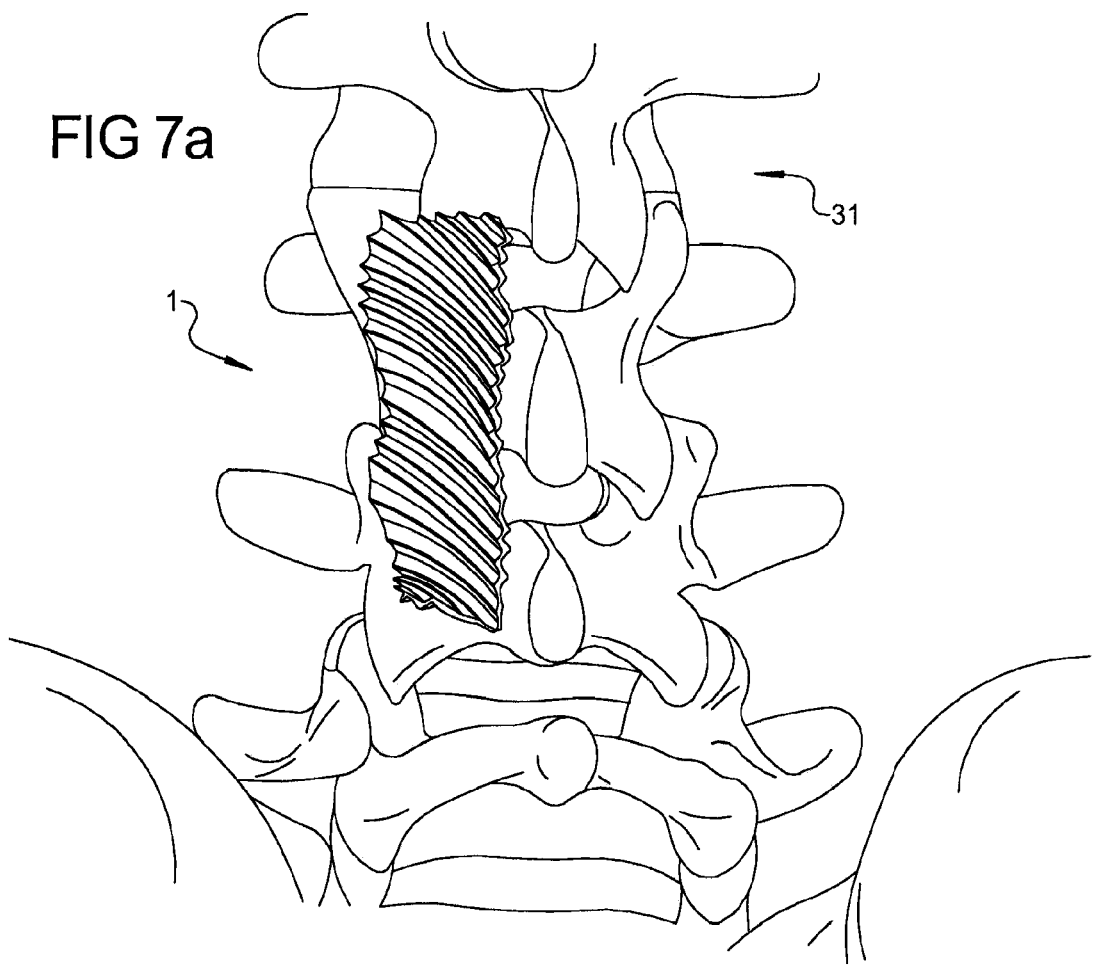
FIGS. 7a-7d are perspective views illustrating methods of use of implantable pliable bone blocks according to principles of the present technology.
Figure 7B:
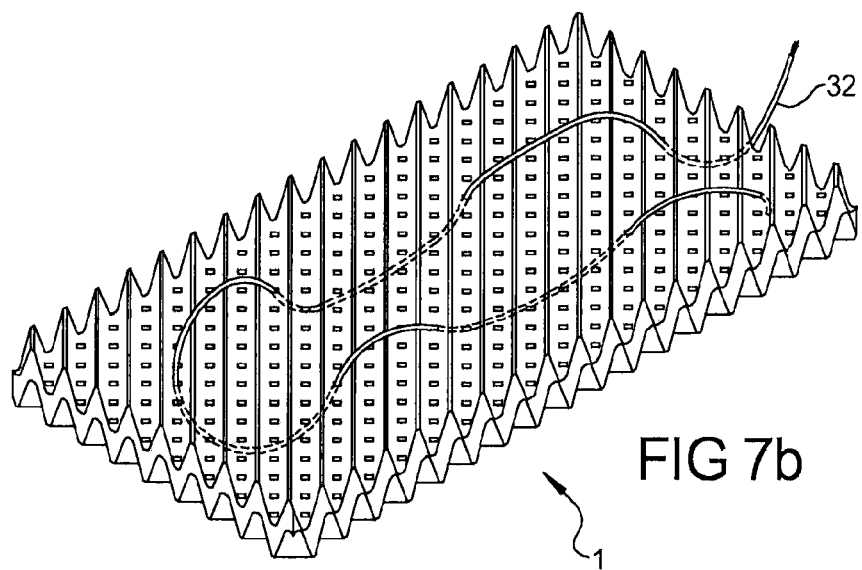
Figure 7C:
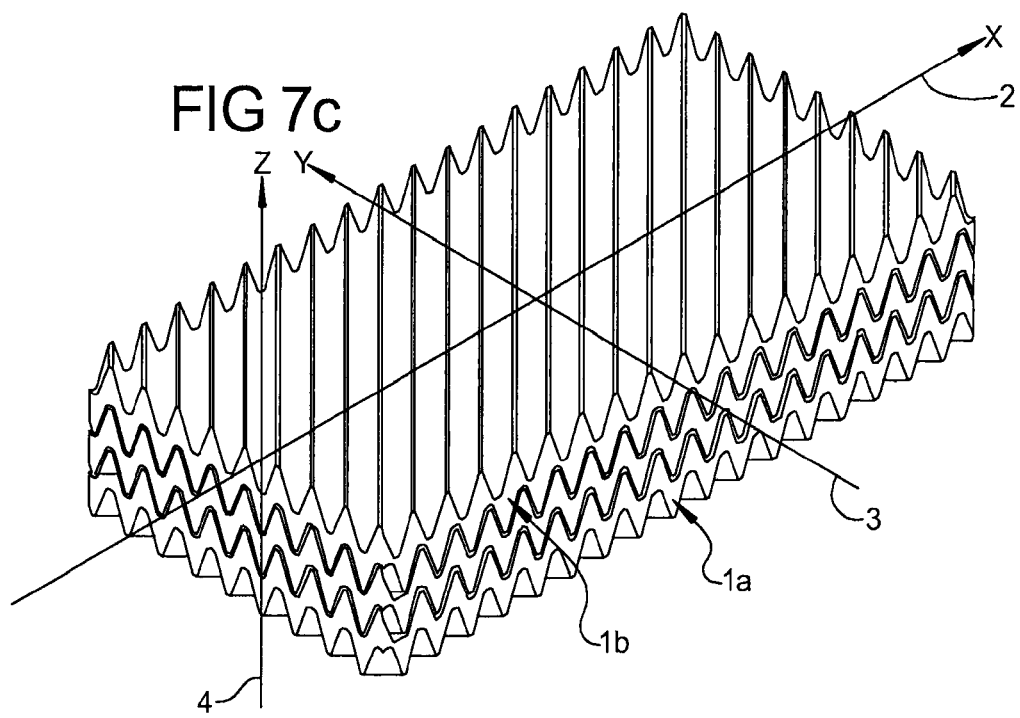
Figure 7D:
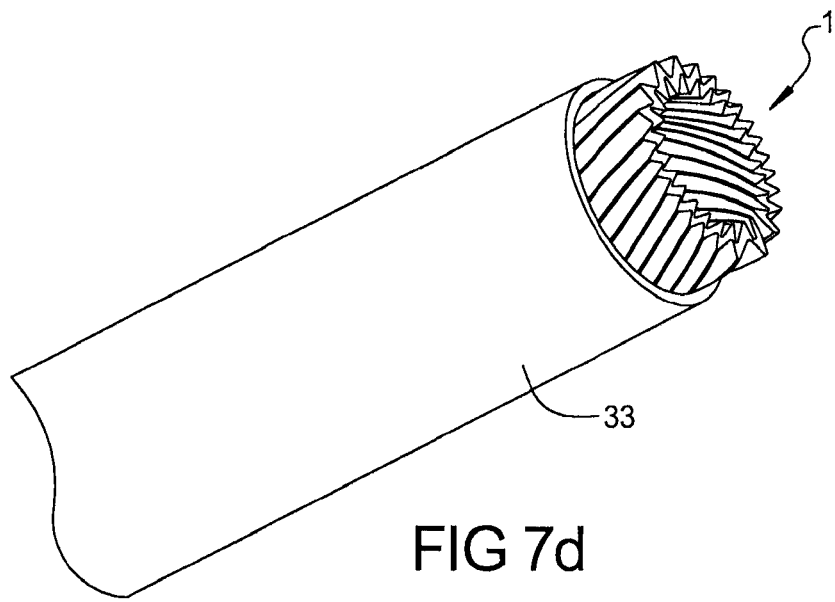

Several exemplary uses of the bone blocks 1 of the present technology are depicted in FIGS. 7a-7d. For example, as depicted in FIG. 7a, the bone block 1 can be implanted along posterolateral gutters in the spine 31. As in FIG. 7b, bone block 1 can be wrapped or laced with an electronic stimulation cathode 32, prior to implantation. This approach can promote bone growth and formation by electronic stimulation. As shown in FIG. 7c, the multiple bone blocks 1a, 1b can be interlocked to make a thicker (along the z-axis 4) construct for implantation, such as for increased rigidity of the implant. As shown in FIG. 7d, a bone block 1 can be collapsed or folded to fit inside a tube or cylinder 33 of at least 10 mm diameter for percutaneous implantation. Cylinders 33 can also be used to fill spinal cages and large bone voids.

Where the bone has been crushed or fragmented, the bone fragments can be "glued" together in its physiological state. The implantable pliable bone block of the present teachings can be used to hold the repaired bone fragments in place while the natural bone matrix regrows and replaces the "glue" that holds the fragment(s) together.

The bone block can also be used to heal compression fractions, such as compression of the tibia. The cortical bone surface can be re-aligned and fixed in place using mechanical fixation and the implantable pliable bone block of the present teachings can be used to fill the void created by the compressive destruction of the bone.

The implantable pliable bone block can also be used to secure pins, screws and other more complicated orthopedic devices that are used to fix bone in place. By immobilizing the fracture using orthopedic hardware and embedding the hardware in bone graft paste, potential voids are filled, thereby expediting new bone formation around the immobilizing or orthopedic device (e.g. a bone screw). In some embodiments, the implantable pliable bone block acts to distribute the force imparted by the screw across a greater surface area, thereby reducing the likelihood of pull out or early bone resorption.

The implantable pliable bone block of the present technology can also be used in arthroplasty procedures of the hip, knee, shoulder and other joints to fix plastic and metal prosthetic parts to living bone. In some embodiments, this approach can be effectively employed in repair of broken hipbones, where a hip prosthesis can be used to reinforce the weight-bearing femoral neck of the femur.

The materials and methods of the present technology are illustrated by the following non-limiting example.

EXAMPLE

A section of solid cortical bone is obtained from a human cadaver, and cut to block dimensions of 25 mm wide by 50 mm long by 5 mm thick. Slot features are cut into the first and second opposing faces of the block, at 45° intersecting angles using a CNC mill. The processed piece of cortical bone is then fully demineralized and freeze dried (<6% residual moisture) for storage/shipping. The product is rehydrated in saline under a vacuum and placed in the posterolateral gutters during a spinal fusion procedure.

Non-limiting Discussion of Terminology:

The headings (such as "Introduction" and "Summary") and sub-headings used herein are intended only for general organization of topics within the present disclosure, and are not intended to limit the disclosure of the technology or any aspect thereof. In particular, subject matter disclosed in the "Introduction" may include novel technology and may not constitute a recitation of prior art. Subject matter disclosed in the "Summary" is not an exhaustive or complete disclosure of the entire scope of the technology or any embodiments thereof. Classification or discussion of a material within a section of this specification as having a particular utility is made for convenience, and no inference should be drawn that the material must necessarily or solely function in accordance with its classification herein when it is used in any given composition.

The examples and other embodiments described herein are intended for purposes of illustration, and are not intended to be limiting in describing the full scope of devices and methods of this technology and, unless explicitly stated otherwise, are not intended to be a representation that given embodiments of this technology have, or have not, been made or tested. Equivalent changes, modifications and variations of specific embodiments, materials, devices and methods may be made within the scope of the present technology, with substantially similar results. Moreover, recitation of multiple embodiments having stated features is not intended to exclude other embodiments having additional features, or other embodiments incorporating different combinations of the stated features.

As used herein, the words "desire" or "desirable" refer to embodiments of the technology that afford certain benefits, under certain circumstances. However, other embodiments may also be desirable, under the same or other circumstances. Furthermore, the recitation of one or more desired embodiments does not imply that other embodiments are not useful, and is not intended to exclude other embodiments from the scope of the technology.

As used herein, the word "include," and its variants, is intended to be non-limiting, such that recitation of items in a list is not to the exclusion of other like items that may also be useful in the materials, compositions, devices, and methods of this technology. Similarly, the terms "can" and "may" and their variants are intended to be non-limiting, such that recitation that an embodiment can or may comprise certain elements or features does not exclude other embodiments of the present technology that do not contain those elements or features.

Although the open-ended term "comprising," as a synonym of non-restrictive terms such as including, containing, or having, is used herein to describe and claim embodiments of the present technology, embodiments may alternatively be described using more limiting terms such as "consisting of" or "consisting essentially of." Thus, for any given embodiment reciting materials, components or process steps, the present technology also specifically includes embodiments consisting of, or consisting essentially of, such materials, components or processes excluding additional materials, components or processes (for consisting of) and excluding additional materials, components or processes affecting the significant properties of the embodiment (for consisting essentially of), even though such additional materials, components or processes are not explicitly recited in this application. For example, recitation of a composition or process reciting elements A, B and C specifically envisions embodiments consisting of, and consisting essentially of, A, B and C, excluding an element D that may be recited in the art, even though element D is not explicitly described as being excluded herein.

As referred to herein, all compositional percentages are by weight of the total composition, unless otherwise specified. Disclosures of ranges are, unless specified otherwise, inclusive of endpoints. Thus, for example, a range of "from A to B" or "from about A to about B" is inclusive of A and of B. Disclosure of values and ranges of values for specific parameters (such as temperatures, molecular weights, weight percentages, etc.) are not exclusive of other values and ranges of values useful herein. It is envisioned that two or more specific exemplified values for a given parameter may define endpoints for a range of values that may be claimed for the parameter. For example, if Parameter X is exemplified herein to have value A and also exemplified to have value Z, it is envisioned that Parameter X may have a range of values from about A to about Z. Similarly, it is envisioned that disclosure of two or more ranges of values for a parameter (whether such ranges are nested, overlapping or distinct) subsume all possible combination of ranges for the value that might be claimed using endpoints of the disclosed ranges. For example, if Parameter X is exemplified herein to have values in the range of 1-10, or 2-9, or 3-8, it is also envisioned that Parameter X may have other ranges of values including 1-9, 1-8, 1-3, 1-2, 2-10, 2-8, 2-3, 3-10, and 3-9.

What is claimed is:

1. An implantable bone block, comprising: a solid block of cortical bone characterized by a length (along an x-axis), width (along a y-axis) and thickness (along a z-axis), having a first face and a second face along the x and y axes on opposite sides of the block, each of the first and second faces having a plurality of substantially linear and substantially parallel slot features wherein the angle of incidence ($a_1$) of the slot features of the first face and the x-axis and the angle of incidence ($a_2$) of the slot features of the second face and the x-axis are such that the slot features of the first face would intersect the slot features of the second face if they were in the same plane, wherein the slot features are characterized by a depth substantially along the z-axis, wherein the sum of depth ($d_1$) of the features on the first face and the depth ($d_2$) of the features on the second face is greater than the thickness of the block.

2. The bone block of claim 1, wherein the bone block is at least about 50% to about 100% demineralized.

3. The bone block of claim 1, wherein the bone block further comprises a bioactive agent.

4. The bone block of claim 3, wherein the bioactive agent is selected from the group consisting of an osteoinductive agent, serum, bone marrow aspirate, hematopoietic stem cells, stromal stem cells, mesenchymal stem cells, endothelial progenitor cells, red blood cells, white blood cells, fibroblasts, reticulacytes, adipose cells, endothelial cells, bone growth factors, extracellularmatrix proteins, hormones, cytokines, cell signaling proteins, platelet concentrate, blood, pharmaceutical actives, and combinations thereof.

5. The bone block of claim 4, comprising an osteoinductive agent selected from the group consisting of transforming growth factor-beta (TGFβ); bone morphogenetic factors (BMPs); platelet-derived growth factors (PDGFs); insulin-like growth factors IGF I and IGF II, fibroblast growth factors (FGFs), vascular endothelial growth factor (VEGF), osteocalcin, osteopontin, and combinations thereof.

6. The bone block of claim 5, wherein the osteoconductive agent is selected from the group consisting of TGFβ-1, TGFβ-2, TGFβ-3, TGFβ-4, and TGFβ-5, and mixtures thereof.

7. The bone block of claim 1, wherein the angles $a_1$ and $a_2$ are each from about 10° to about 35°.

8. The bone block of claim 7, wherein the distance between the slot features on each of the first face and the second face is from about 0.5 mm to about 3 mm.

9. The bone block of claim 1, wherein the angles $a_1$ and $a_2$ are each from about 35° to about 55°.

10. The bone block of claim 1, wherein the angles $a_1$ and $a_2$ are each from about 50° to about 75°.

11. The bone block of claim 1, wherein the bone block is lyophilized.

12. The bone block of claim 11, wherein the bone block becomes pliable when hydrated.

13. The bone block of claim 1, wherein a plurality of holes having a diameter of from about 0.5 mm to about 2 mm are formed at the intersections of the slot features of the first face and the slot features of the second face.

14. The bone block of claim 1, configured for percutaneous implantation; posterolateral spinal fusions; filling interbody cages; external or internal bone graft containment; or repair or replacement of ethmoid, frontal, nasal, occipital, parietal, temporal, mandible, maxilla, zygomatic, cervical vertebra, thoracic vertebra, lumber vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones.

15. A method for making an implantable bone block for application to a bone surface of a human or animal subject, comprising:
   a) forming a block from cortical bone, the block by a length (along an x-axis), width (along a y-axis) and thickness (along a z-axis), having a first face and a second face along the x and y axes on opposite sides of the block;
   b) demineralizing the block;
   c) forming a plurality of slots on the first face of the bone block;
   d) forming a plurality of slots on the second face of the bone block;
   e) wherein the angle of incidence ($a_1$) of the slot features of the first face and the x-axis and the angle of incidence ($a_2$) of the slot features of the second face and the x-axis are such that the slot features of the first face would intersect the slot features of the second face if they were in the same plane; and the slot features are characterized by a depth substantially along the z-axis, wherein the sum of depth ($d_1$) of the features on the first face and the depth ($d_2$) of the features on the second face is greater than the thickness of the block, such that a plurality of holes having a diameter of from about 0.5 mm to about 2 mm are formed at the intersections of the slot features of the first face and the slot features of the second face.

16. The bone block of claim 15, wherein the angles $a_1$ and $a_2$ are each from about 10° to about 35°.

17. The bone block of claim 15, wherein the angles $a_1$ and $a_2$ are each from about 35° to about 55°.

18. The bone block of claim 15, wherein the angles $a_1$ and $a_2$ are each from about 50° to about 75°.

19. The method of claim 15, wherein the cortical bone block is at least about 50% to about 100% demineralized.

20. The method of claim 15, further comprising depositing a bioactive agent over a surface of the bone block.

21. The method of claim 20, wherein the bioactive agent is selected from the group consisting of an osteoinductive agent, serum, bone marrow aspirate, hematopoietic stem cells, stromal stem cells, mesenchymal stem cells, endothelial progenitor cells, red blood cells, white blood cells, fibroblasts, reticulacytes, adipose cells, endothelial cells, bone growth factors, extracellularmatrix proteins, hormones, cytokines, cell signaling proteins, platelet concentrate, blood, pharmaceutical actives, and combinations thereof.

22. The method of claim 20, wherein the bioactive agent is selected from the group consisting of transforming growth factor-beta (TGFβ); bone morphogenetic factors (BMPs); platelet-derived growth factors (PDGFs); insulin-like growth factors IGF I and IGF II, fibroblast growth factors (FGFs), vascular endothelial growth factor (VEGF), osteocalcin, osteopontin, and combinations thereof.

23. The method of claim 22, wherein the bioactive agent is selected from the group consisting of TGFβ-1, TGFβ-2, TGFβ-3, TGFβ-4, and TGFβ-5, and mixtures thereof.

24. The method of claim 15, further comprising configuring the implantable pliable bone block for percutaneous implantation; posterolateral spinal fusions;
   filling interbody cages; or repair or replacement of ethmoid, frontal, nasal, occipital, parietal, temporal, mandible, maxilla, zygomatic, cervical vertebra, thoracic vertebra, lumber vertebra, sacrum, rib, sternum, clavicle, scapula, humerus, radius, ulna, carpal bones, metacarpal bones, phalanges, ilium, ischium, pubis, femur, tibia, fibula, patella, calcaneus, tarsal bones, or metatarsal bones.

25. The method of claim 15, further comprising lyophilizing the block.

* * * * *